United States Patent [19]

Cash

[11] Patent Number: 4,778,814
[45] Date of Patent: Oct. 18, 1988

[54] METHOD OF TREATING OCULAR ALLERGY BY TOPICAL APPLICATION OF A 2-SUBSTITUTED-1,2-BENZISOSELENAZOL-3(2H)-ONE

[75] Inventor: William D. Cash, Riverside, Conn.

[73] Assignee: Ciba-Geigy Corporation, Ardsley, N.Y.

[21] Appl. No.: 27,300

[22] Filed: Mar. 18, 1987

[51] Int. Cl.$^4$ ............................................. A61K 31/41
[52] U.S. Cl. ..................................... 514/359; 514/912
[58] Field of Search ................................. 514/359, 912

[56] References Cited

U.S. PATENT DOCUMENTS

| | | | |
|---|---|---|---|
| 4,352,799 | 10/1982 | Renson et al. | 424/244 |
| 4,397,858 | 8/1983 | Welter et al. | 424/270 |
| 4,418,069 | 11/1983 | Welter et al. | 548/100 |
| 4,454,068 | 6/1984 | Welter et al. | 260/239 R |
| 4,550,168 | 10/1985 | Welter et al. | 546/270 |
| 4,711,961 | 12/1987 | Welter et al. | 548/121 |

FOREIGN PATENT DOCUMENTS

| | | |
|---|---|---|
| 44453 | 1/1982 | European Pat. Off. |
| 3616923 | 11/1987 | Fed. Rep. of Germany . |

OTHER PUBLICATIONS

Chem. Abst. 106:43,658v (1987)–Van Dyke et al.

Chem. Abst. 106:102,292w & 106:102293x (1987)–Welter et al.

*Primary Examiner*—Douglas W. Robinson
*Attorney, Agent, or Firm*—Irving M. Fishman

[57] ABSTRACT

A method of treating an ocular allergy in a mammal comprising the topical application of an effective anaphylactic inhibiting amount of a compound of the formula:

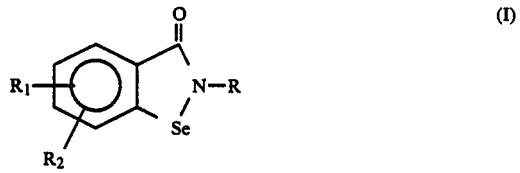

(I)

wherein
R is phenyl or phenyl substituted lower alkyl, the phenyl group of each being unsubstituted or substituted by halo, lower alkyl, lower alkoxy, trifluoromethyl, nitro, di-loweralkylamino, cyano, carboxy, methylenedioxy, loweralkoxycarbonyl, carboxyloweralky, or loweralkoxycarbonyl-lower alkyl, or R is cycloalkyl of 5 to 10 carbon atoms; and
$R_1$ and $R_2$ are independently hydrogen, halo, lower alkyl, lower alkoxy, hydroxy, trifluoromethyl, or nitro or $R_1$ and $R_2$ taken together are methylenedioxy; to the eye of said mammal in need of the same.

2 Claims, No Drawings

METHOD OF TREATING OCULAR ALLERGY BY TOPICAL APPLICATION OF A 2-SUBSTITUTED-1,2-BENZISOSELENAZOL-3(2H)-ONE

BACKGROUND OF THE INVENTION

The instant invention relates to a method of treating an ocular allergy in a warm blooded mammal, including man, by topically applying an effective anaphylactic inhibiting amount of a 2-aryl, aralkyl or cycloalkyl-1,2-benzisoselenazol-3(2H)-one to the eye of said mammal in need of the same.

The compounds useful in the practice of the present invention are known and are described as possessing anti-inflammatory properties, as see U.S. Pat. Nos. 4,352,799; 4,397,858; 4,418,069; and 4,454,068 the disclosures of which are incorporated by reference herein.

It is now surprisingly been discovered that, in addition to the aforementioned anti-inflammatory properties, such 2-substituted-1,2-benzoisoselenazol-3(2H)-one compounds surprisingly and unexpectedly possesses the property of inhibiting an allergic ocular condition upon topical application to the eye of the host.

It is accordingly an object of the present invention to provide a method for treating ocular allergies.

It is further object of the present invention to provide a method for inhibiting ocular anaphylactic reactions to environmental dusts, pollens, industrial irritants, and the like by topically administering to a mammalian host susceptible to such reactions an effective inhibiting amount of an ocular compatable composition containing a 2-substituted-1,2-benzisoselenazol-3(2H)-one.

It is yet a further object of the present invention to provide ocular compositions for use in such methods.

These and other objects of the present invention are apparent from the following detailed description.

DETAILED DESCRIPTION OF THE INVENTION

One embodiment of the present invention relates to a method of treating an ocular allergy in a mammal comprising the topical application to the eye of said mammal in need of the same an effective anaphylactic inhibiting amount of a compound of the formula

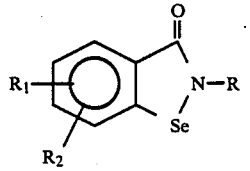

wherein
R is phenyl or phenyl substituted lower alkyl, the phenyl group of each being unsubstituted or substituted by halo, lower alkyl, lower alkoxy, trifluoromethyl, nitro, di-loweralkylamino, cyano, carboxy, methylenedioxy, lower alkoxycarbonyl, carboxyloweralkyl or lower alkoxycarbonyl substituted lower alkyl, or R is cycloalkyl of 5 to 10 carbon atoms; and
$R_1$ and $R_2$ are independently hydrogen, halo, lower alkyl, lower alkoxy, hydroxy, trifluoromethyl or nitro, or $R_1$ and $R_2$ are adjacent and taken together are methylenedioxy.

The term, anaphylactic, as used herein is used in its broadest sense to include all forms of allergic hypersensitivity.

Preferred are those compounds of formula I wherein R is said phenyl or substituted phenyl and $R_1$ and $R_2$ are hydrogen. Most preferred R is phenyl and $R_1$ and $R_2$ are hydrogen.

By "lower" as in lower alkyl, or lower alkoxy, etc. is meant alkyl of 1 to 4 carbon atoms, preferably 1 to 2 carbon atoms.

By "halo" is meant preferably chloro, bromo or fluoro, most preferably chloro.

The compounds can be prepared by methods known, per se. Thus, the compounds of formula I can be prepared by reacting a compound of the formula

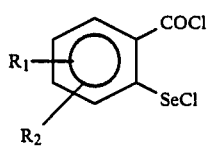

with an amine of the formula

under conventional ring closure conditions, e.g. at a temperature between about −20° C. to about 20° C., optionallyin the presence of an organic tertiary amine, such as a tri-lower alkyl amine such as triethylamine, or pyridine, in an inert diluent, such as tetrahydrofuran or carbon tetrachloride, and recovering the product.

The compounds of formula I and their preparation are more fully described in U.S. Pat. Nos. 4,352,799; 4,397,858; 4,418,069 and 4,454,068, the disclosures of which are incorporated herein.

Advantageously the compound of formula is topically administered to the eye in the form of an aqueous solution, suspension, ointment or cream or in the form of a controlled release lozenge or within a rate controlled membrane containing device for placement within the conjunctival sac. Preferably, the compound is administered in the form of an aqueous solution or suspension containing between about 0.002 to about 5 percent by weight, most preferably between about 0.004 and about 2% by weight, of a compound of formula I.

In order to enhance the solubility of the active agent of formula I in the ocular composition, pharmaceutically acceptable eye compatable adjuvants, such as ethoxylated castor oil, propylene glycol, glycerine, low molecular weight polyethylene glycol, poloxamers and the like, in amounts between about 0.01 and about 30 weight percent, based upon the total weight of the composition, may be employed. Also, conventional pharmaceutical excipients, such as sodium borate, boric acid, tromethamine, potassium chloride, sodium phosphate, sodium citrate and the like may be present in amounts between about 0.01 and 3 weight percent, based upon the total weight of the composition. In addition, opthamologically acceptable preservatives, such as sodium edetate, benzalkonium chloride, sorbic acid and the like may be present in amounts between about 0.005 and about 0.1 weight percent, based upon the total weight of composition. If desired, the resulting composition osmolality may be adjusted, e.g. with sodium chloride or the like, such that the composition is substantially isotonic. Preferably, the pH of the aqueous composition is between about 5 and about 7.

While not being bound by any specific mode of ocular anaphylactic inhibition, it is believed that the instant compounds operate to inhibit mass cell degranulation in the ocular region, thereby inhibiting the release of histamine. Moreover, it is believed that the compounds also inhibit leucocyte cell infiltration.

The following Example is merely for illustrative purposes and is not intended to limit the invention. All parts are parts by weight unless otherwise indicated.

EXAMPLE 1

0.055 Mg of micronized 2-phenyl-1,2-benzisoselenazol-3(2H)-one, 50 grams of polyethoxylated high purity castor oil (Cremophor ® EL, BASF Wyandotte Corp.), 19 grams of boric acid and 0.75 grams of tromethamine are combined with sufficient water to provide one liter of solution. The solution has a pH of between 5.2 and 5.5 and contains the 2-phenyl-1,2-benzisoselenazol-3(2H)-one in a concentration of 0.2 micromolar. One to two drops of the solution (about 50 to about 100 microliters) can be placed into each eye of the mammalian host.

What is claimed is:

1. A method of treating an ocular allergy in a mammal comprising topically applying to the eye of said mammal in need thereof an amount effective to inhibit ocular anaphylactic reaction of a compound of the formula

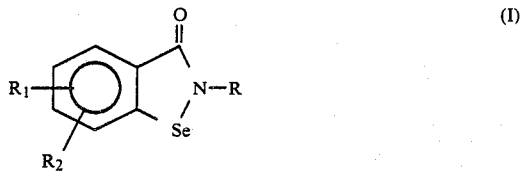

wherein
R is phenyl or phenyl substituted lower alkyl, wherein the phenyl group of each is unsubstituted or substituted by halo, lower alkyl, lower alkoxy, trifluoromethyl, nitro, di-lower alkylamino, cyano, carboxy, methylenedioxy, lower alkoxycarbonyl, carboxy substituted lower alkyl, or lower alkoxycarbonyl substituted lower alkyl, or R is cycloalkyl of 5 to 10 carbon atoms; and
$R_1$ and $R_2$ are independently hydrogen, halo, lower alkyl, lower alkoxy, hydroxy, trifluoromethyl or nitro, or $R_1$ and $R_2$ taken together are methylenedioxy.

2. A method according to claim 1 wherein R is phenyl and both $R_1$ and $R_2$ are hydrogen.

* * * * *